(12) United States Patent
Kudlicki et al.

(10) Patent No.: US 7,163,793 B2
(45) Date of Patent: *Jan. 16, 2007

(54) NUCLEASE INHIBITOR COCKTAIL

(75) Inventors: W. Antoni Kudlicki, Austin, TX (US); Matthew M. Winkler, Austin, TX (US); Brittan L. Pasloske, Austin, TX (US)

(73) Assignee: Ambion, Inc., Austin, TX (US)

( * ) Notice: Subject to any disclaimer, the term of this patent is extended or adjusted under 35 U.S.C. 154(b) by 278 days.

This patent is subject to a terminal disclaimer.

(21) Appl. No.: 10/675,860

(22) Filed: Sep. 30, 2003

(65) Prior Publication Data

US 2005/0026284 A1   Feb. 3, 2005

Related U.S. Application Data

(63) Continuation of application No. 09/669,301, filed on Sep. 25, 2000, now Pat. No. 6,664,379.

(60) Provisional application No. 60/155,874, filed on Sep. 24, 1999.

(51) Int. Cl.
*C12Q 1/68* (2006.01)
*C07K 1/00* (2006.01)
*C07K 14/00* (2006.01)
*C07K 16/00* (2006.01)
*C12P 21/08* (2006.01)

(52) U.S. Cl. .................. 435/6; 530/350; 530/387.1; 530/387.9

(58) Field of Classification Search .................. 435/6; 536/23.1, 24.3; 530/350, 387.1, 387.9
See application file for complete search history.

(56) References Cited

U.S. PATENT DOCUMENTS

| 5,972,613 A | 10/1999 | Somack et al. ............... 6/435 |
| 5,973,137 A | 10/1999 | Heath ........................ 536/25.4 |
| 6,110,968 A | 8/2000 | Bucala et al. ............... 514/482 |
| 6,869,604 B1* | 3/2005 | Rybak et al. ............. 424/94.61 |

OTHER PUBLICATIONS

Devaux et al., Molecular and Cellular Biochemistry 74 : 117-128 (1987).*
Worthington Nuclease, Micrococcal (S7) from http://www.worthington-biochem.com/NFCP/default.html 8 pages.*
Allewell and Sama, "The effect of ammonium sulfate on the activity of ribonuclease a," *Biochem. Biophys.* ACTA, 341:484-488, 1974.
Blackburn et al., "Ribonuclease inhibitor from human placenta: interaction with derivatives of ribonuclease A," *J. Biol. Chem.* 252:12488-12493, 1977.
Blumberg, "Creating a ribonuclease-free environment," *Methods Enzymol.* 152:20-24, 1987.
Cazenave, "Idiotypic-anti-idiotypic regulation of antibody sythesis inrabbits," *Proc. Natl. Acad. Sci. USA*, 74:5122-5125, 1977.

Chirgwin, et al., "Isolation of biologically active ribonucleic acid from sources enriched in ribonuclease," *Biochemistry* 18:5294-5299, 1979.
Chomczynski and Sacchi, "Single step method of rna isolation by acid guanidinium thiocyanate-phenol-chloroform extraction," *Anal. Biochem.* 162:156-159, 1987.
Chomczynski, "Solubolization in formamide protects rna from degradation," *Nucleic Acids Res.* 20:3791-3792, 1992.
Coburn and Mackie, "Overxpression, purification, and properties of escherichia coli ribonuclease II," *J. Biol. Chem.* 271:1048-1053, 1996.
Gilleland and Hockett Jr., "Stability of rna molecules stored in gitc," *Biotechniques* 25:944-948, 1998.
Jocoli and Ronald, "Inhibition of ribonuclease activity by bentonite," *Can. J. Biochem.* 51:1558-1565, 1973.
Jones, "On the efficacy of commonly used ribonuclease inhibitors," *Biochem. Biophys. Res. Commun.* 69:469-474, 1976.
Lee et al., "The use of immobilized anti-ribonuclease antibodies in the isolation of polyribosomes," *Immunochemistry*, 9:210-213, 1972.
Lin, "Inactivation of pancreatic ribonuclease with hydroxylamine-oxygen-cupric ion," *Biochim. et Biophys. Acta* 263:680-682, 1972.
Mendelsohn and Young, "Efficacy of sodium dodecyl sulfate, diethyl pyrocarbonate, proteinase k and heparin using a sensitive ribonuclease assay," *Biochim. et Biophys. Acta* 519:461-473, 1978.
Murphy et al., "A potent, cost-effective rnase inhibitor," *Biotechniques* 18:1068-1073, 1995.
O'Leary, "Reducing the Impact of Endogenous Ribonucleases on Reverse Transcription-PCR Assay Systems," *Clinical Chemistry*, 45(4):449-450, 1999.

(Continued)

*Primary Examiner*—Ethan Whisenant
(74) *Attorney, Agent, or Firm*—Fulbright & Jaworski L.L.P.

(57) ABSTRACT

Methods and compositions for inhibiting and/or inactivating nucleases by employing nuclease inhibitors are provided. The nuclease inhibitors comprise anti-nuclease antibodies and non-antibody nuclease inhibitors. The anti-nuclease antibodies of the present invention may be a polyclonal or monoclonal antibodies, and may be anti-ribonuclease antibodies, anti-deoxyribonuclease antibodies, or antibodies to non-specific nucleases. A preferred embodiment comprises at least two nuclease inhibitors, and is referred to as a nuclease inhibitor cocktail. In some specific embodiments, the invention concerns methods of performing in vitro translation comprising obtaining a first nuclease inhibitor, which inhibitor is further defined as an anti-nuclease antibody, and placing the anti-nuclease antibody in an in vitro translation reaction. In many cases, the in vitro translation reaction comprises at least one nuclease, which may be a ribonuclease, a deoxyribonuclease, or a nonspecific nuclease. The invention also relates to kits for the performance of various microbiological procedures, which kits comprise the nuclease inhibitors described herein.

42 Claims, No Drawings

OTHER PUBLICATIONS

Pelham and Jackson, "An efficient mRNA dependent translation system for reticulocyte lysates," *Eur. J. Biochem.* 67:247-256, 1976.

Russo and Shapiro, "Potent inhibition of mammalian ribonucleases by 3' 5'-pyrophosphate-linked nucleotides," *J. Biol. Chem.* 274:14,902-14,908, 1999.

Sambrook, et al., "Molecular cloning, a laboratory manual," pp. 7.16-7.52, 1989.

Spackman et al., "The Disulfide Bonds of Ribonuclease," *J. Biol. Chem.* 235:648-659, 1960.

Spicler and Mackie, "Action of rnase ii and polynucleotide phosphorylase against rnas containing stem-loops of defined structure," *J. Bacteriology* 182(9): 2422-2427, 2000.

Trent et al., "A comparison of new world alphaviruses in the western equine encephalomyelitis complex by immunochemical and oligonucleotide fingerprint techniques," *J. Gen. Virol.*, 47:261-282, 1980.

Wolf et al., "A mechanism of the irreversible inactivation of bovine pancreatic ribonuclease by diethylpyrocarbonate ," *Eur. J. Biochem.* 13:519-525, 1970.

Wu, et al., "Methods in Gene Biotechnology," CRC Press, Boca Raton, FL, pp. 29-56, 1997.

Zale and Klibanov, "Why does ribonuclease irreversibly inactivate at high temperatures?," *Biochemistry* 25:5432-5444, 1986.

Co-Pending U.S. Appl. No. 10/786,875, filed Feb. 25, 2004.

Pending PCT Application No. PCT/US2004/005663 filed Feb. 25, 2004.

Pending U.S. Appl. No. 60/547,721, filed Feb. 25, 2004.

Feldman et al., "Interaction of ribonuclease A with estrogen receptor from rat mammary tumor MTW9*", *The Journal of Biological Chemistry*, 258:5001-5004, 1983.

Fett, et al., "A monoclonal antibody to human angiogenin. Inhibition of ribonucleolytic and angiogenic activities and localization of the antigenic epitope", *Biochemistry*, 33:5421-5427, 1994.

Fransen et al., "Isolation of HIV-1 RNA from plasma: evaluation of seven different methods for extraction (part two)", *Journal of Virological Methods*, 76:153-157, 1998.

Shen et al., "Poly[G] improved protein productivity of cell-free translation by inhibiting mRNase in wheat germ extract", *Journal of Biotechnology*, 75:221-228, 1999.

Simpson et al., "An improved method for mRNA isolation and characterization of in vitro translation products by western blotting", *Gene*, 56:161-171, 1987.

\* cited by examiner

NUCLEASE INHIBITOR COCKTAIL

BACKGROUND OF THE INVENTION

This application is a continuation of U.S. application Ser. No. 09/669,301, filed Sep. 25, 2000 now U.S. Pat. No. 6,664,379, which claims the benefit of U.S. Provisional Patent Application Ser. No. 60/155,874 filed Sep. 24, 1999. The entire text of these applications are specifically incorporated by reference herein without disclaimer.

FIELD OF THE INVENTION

The present invention relates generally to the field of molecular biology. More particularly, it concerns the inhibition and/or inactivation of nucleases which can degrade DNA (deoxyribonucleases) and/or RNA (ribonucleases). Inhibition and/or inactivation of nucleases in the present invention employs at least one, and in many cases at least two nuclease inhibitors. These nuclease inhibitors include anti-nuclease antibodies and non-antibody nuclease inhibitors.

DESCRIPTION OF RELATED ART

The quality of an RNA preparation greatly affects the results obtained when analyzing it by a number of different molecular biology techniques such as northern blotting, ribonuclease protection assays and RT-PCR (Reverse Transcriptase-Polymerase Chain Reaction). Degraded RNA will produce a lower signal than in an equivalent intact RNA sample.

RNA is much more susceptible to degradation than DNA (Sambrook et al., 1989). RNA is readily hydrolyzed when exposed to conditions of high pH, metal cations, high temperatures and contaminating ribonucleases. A major cause of RNA degradation is ribonuclease contamination, and this must be guarded against in virtually all RNA-related procedures, including RNA isolation, mRNA purification, RNA storage, northern blotting, nuclease protection assays, RT-PCR, in vitro transcription and/or translation and RNA diagnostics. In addition to the endogenous ribonucleases from cells and tissues, finger grease and bacteria and/or fungi in airborne dust particles are common sources of ribonuclease. To minimize ribonuclease contamination, appropriate precautions must be followed when handling RNA (Blumberg, 1987; Wu, 1997).

Ribonucleases are difficult to inactivate. For example, bovine pancreatic ribonuclease A (RNase A) has no activity at 90° C. However, if the enzyme is quickly cooled to 25° C., the activity is fully restored. This process is known as reversible thermal denaturation. If the RNase A is incubated at 90° C. over time, then decreasing fractions of the activity are recovered at 25° C. This process is known as irreversible thermoinactivation. At 90° C., it takes several hours to inactivate RNase A (Zale and Klibanov, 1986). Much of the lost activity is attributed to disulfide interchange (Zale and Klibanov, 1986). Further, the inventors and others have found that ribonucleases can even withstand autoclaving (121° C., 15 psi, 15 minutes) to some degree. Spackman et al. (1960) tested the stability of RNase A and concluded that it was stable to heat, extremes of pH, and the protein denaturant, urea, results emphasizing the difficulty researchers have had inactivating ribonucleases. For the above reason, a variety of methods other than heating have been developed to inhibit or inactivate ribonucleases. These methods, and their disadvantages, are described below.

In one method of destroying RNases, diethyl pyrocarbonate (DEPC) is added to final concentration of 0.1% to molecular biology reagents, glassware or electrophoresis apparatus, followed by incubating at 37° C. for several hours and then autoclaving for 15–20 minutes to destroy the DEPC (Wolf et al., 1970). DEPC reacts with the α-amino-groups of lysine and the carboxylic groups of aspartate and glutamate both intra- and intermolecularly (Wolf et al., 1970). This chemical reaction forms polymers of the ribonuclease. However, there are several disadvantages to using DEPC: (1) It is a possible carcinogen and is hazardous to humans; (2) some commonly used molecular biology reagents such as Tris react with and inactivate DEPC; (3) treatment of samples with DEPC is time-consuming; (4) DEPC reacts with the adenine residues of RNA, rendering it inactive in in vitro translation reactions (Blumberg, 1987) and 5) If all of the DEPC is not destroyed by autoclaving, remaining trace amounts may inhibit subsequent enzymatic reactions.

Traditionally, RNA is stored in DEPC-treated water or TE buffer. However, the RNA is not protected from degradation if the sample or the storage solution has ε-minor ribonuclease contamination. It has been suggested that RNA be stored in ethanol, formamide, or guanidinium to protect an RNA sample from degradation because these environments minimize ribonuclease activity (Chomczynski, 1992; Gilleland and Hockett, 1992). The obvious disadvantage is that the RNA sample cannot be directly utilized for analysis or enzymatic reactions unless the ethanol, formamide, or guanidinium is removed.

Guanidinium thiocyanate is commonly used to inhibit RNases during RNA isolation (Chomczynski and Sacchi, 1987; Sambrook et al., 1989). A high concentration of guanidinium thiocyanate combined with β-mercaptoethanol is used to isolate RNA from tissues, even those that are rich in ribonucleases, such as pancreas (Chirgwin et al., 1979). Guanidinium is an effective inhibitor of most enzymes due to its chaotropic nature. However, if RNA is dissolved in guanidinium, then it must first be purified from the guanidinium prior to being used in an enzymatic reaction.

Vanadyl-ribonucleoside complexes (VRC) may be used to inhibit RNases during RNA preparation (Berger and Birkenmeier, 1979). The drawback to using VRC, is that VRC strongly inhibits the translation of mRNA in cell-free systems and must be removed from RNA samples by phenol extraction (Sambrook et al., 1989).

Favaloro et al. (1980) employed macaloid, a clay, to absorb RNases. A limitation of this method is that it is difficult to completely remove the clay from RNA samples. Other reagents have been used to inhibit ribonucleases including sodium dodecylsulfate (SDS), ethylenediamine tetraacetic acid (EDTA), proteinase K, heparin, hydroxylamine-oxygen-cupric ion, bentonite and ammonium sulfate (Allewell and Sama, 1974; Jocoli and Ronald, 1973; Lin, 1972; Jones, 1976; Mendelsohn and Young, 1978). None of these reagents are strong inhibitors alone. Like many of the RNase inhibitors already described, although these chemicals inhibit RNase activity, they also may inhibit other enzymes such as reverse transcriptase and DNase I. Therefore, the RNA must be purified away from the inhibitory reagent(s) before it can be subjected to other enzymatic processes.

Two types of proteinaceous RNase inhibitors are commercially available: human placental ribonuclease inhibitor (Blackburn et al., 1977) and PRIME Inhibitor™ (Murphy et al., 1995). RNases of the class A family bind tightly to these protein inhibitors and form noncovalent complexes that are enzymatically inactive. The major disadvantage of these inhibitors is that they have a narrow spectrum of specificity. They do not inhibit other classes of RNases. Another disadvantage when using placental ribonuclease inhibitor is that it denatures within hours at 37° C., releasing the bound ribonuclease.

Heat has been used to inactivate RNase A by mediating the breakage of disulfide bonds. Zale and Klibanov (1986) performed inactivation of RNase A at 90° C. and pH 6.0 for 1 hour, which induced the following chemical changes: disulfide interchange, β-elimination of cysteine residues, and deamidation of asparagine. This type of heat treatment did not completely inactivate the ribonuclease. A major disadvantage is that a long-term, high-temperature treatment (90–100° C.) is incompatible with RNA. Such treatment promotes the hydrolysis of RNA. In fact, the inventors have found that total RNA incubated at 65° C. for several hours is almost completely degraded. Thus, treating an RNase sample with extreme heat to inactivate ribonucleases will mediate the destruction of the RNA which the user is trying to protect.

SUMMARY OF THE INVENTION

The present invention provides methods and compositions for rapidly inhibiting and/or inactivating nucleases. In some aspects, the present invention relates to methods for inhibiting nucleases with one or more nuclease inhibitors and compositions comprising nuclease inhibitors that can be used in such methods.

Such methods may comprise: a) obtaining at least a first nuclease inhibitor; b) obtaining at least a second nuclease inhibitor; c) obtaining a composition; and d) admixing the nuclease inhibitors and the composition. Under circumstances where there are nucleases present in the composition, those nucleases are inhibited to some extent. Note that complete inactivation or inhibition of nucleases is not required to obtain benefit from the invention. Further, note that these aspects of the invention are not limited to cases where one knows that there is a nuclease present in the composition. Therefore, it is entirely within the scope of the invention to use the inhibitors disclosed herein to treat a composition which may have nucleases in it, or even a composition which a research is confident does not have nucleases in it, but which the researcher wishes to treat out of an abundance of caution. In some embodiments, the composition will have a nuclease present, for example a ribonuclease (RNase), deoxyribonuclease (DNase), a non-specific nuclease, or a combination of two or more of these, as described elsewhere in this specification. Some embodiments involve inhibition of RNase, DNase, a non-specific nuclease, or a combination thereof.

In some broad aspects, the present invention relates to methods and compositions for inhibiting or inactivating nucleases using at least two nuclease inhibitors, which can include, in various embodiment, anti-nuclease antibodies and non-antibody nuclease inhibitors. A composition comprising at least two nuclease inhibitors is referred to herein as a "nuclease inhibitor cocktail," and includes but is not limited to, the specific inhibitors disclosed elsewhere in this specification. The composition treated according to the methods of the invention can be any composition that one of skill in the art would find it beneficial to treat in order to prevent nuclease activity in the composition. In most cases, the composition will be liquid, although solid compositions such as a matrix comprising immobilized nuclease inhibitor may be treated as well. In some preferred embodiments, the composition is a reagent used in molecular biology.

The methods of the invention frequently involve the preparation of a nuclease inhibitor cocktail by the mixing of the first and second nuclease inhibitors. Such a cocktail may be mixed with the composition at any time. For example, the cocktail may be prepared and then relatively immediately mixed with the composition. Alternatively, the cocktail may be prepared in advance. In many cases, the cocktail may be prepared and provided as a commercial product to a researcher, and the researcher practices the invention by obtaining the first and second nuclease inhibitors in the form of the cocktail and then admixing the cocktail with the composition.

In many embodiments of the application, the composition comprises a nucleic acid, for example, DNA or RNA. In some embodiments, the composition comprises RNA that has been purified. For example he composition is further defined as an in vitro translation reaction or a transcription reaction. In some, more specific embodiments, the composition comprises both DNA and RNA. In additional embodiments, the composition is or comprises a reagent used in molecular biology. Exemplary such reagents can be water, tris-EDTA buffer (TE), sodium chloride/sodium citrate buffer (SSC), MOPS/sodium acetate/EDTA buffer (MOPS), Tris buffer, ethylenediamine tetraacetic acid (EDTA), nucleic acid hybridization buffer, sodium acetate buffer, DNase I digestion buffer, transcription buffer, reverse transcription buffer, cell free extract for in vitro translation, in situ hybridization buffer, or nucleic acid storage buffer/solution.

In some preferred embodiments, the first nuclease inhibitor or the second nuclease inhibitor is an anti-nuclease antibody. Such antibodies can be a polyclonal or monoclonal antibodies, with some presently preferred commercial embodiments of the invention employing polyclonal antibodies. The anti-nuclease antibodies may be anti-ribonuclease antibodies, anti-deoxyribonuclease antibodies, or antibodies to non-specific nucleases. The invention may comprise the use of any number of anti-nuclease antibodies with various specificities. The invention includes the use of a mixture of two anti-nuclease antibodies that each inhibit a different nuclease. However, mixtures of three, four, or more anti-nuclease antibodies, each of which inhibit different or the same nucleases, may be used.

Many embodiments involve one or more anti-ribonuclease antibodies. Such anti-ribonuclease antibodies may be an antibody capable of binding to one or more of RNase A, a member of the RNase A family, RNase B, RNase C, RNase 1, RNase T1, RNase T2, RNase L, a member of the RNase H family, a member of the angiogenin RNase family, eosinophil RNase, a micrococcal nuclease, a member of the mammalian ribonuclease 1 family, a member of the ribonuclease 2 family, a messenger RNA ribonuclease, 5'-3' exoribonuclease, 3'-5' exoribonuclease, a decapping enzyme, a deadenylase, RNase P, RNase III, RNase E, RNase I,I*, RNase HI, RNase HII, RNase M, RNase R, RNase IV, F; RNase P2,O, PIV, PC, RNase N, RNase II, PNPase, RNase D, RNase BN, RNase T, RNase PH, OligoRNase, RNase R, RNase H, RNase Sa, RNase F1, RNase U2, RNase Ms, RNase St, or RNase P. Some presently preferred anti-ribonuclease antibodies are those that inhibit one or more members of the RNase A family, for example an anti-RNase A antibody. Others are anti-RNase 1 antibodies and anti-RNase T1 antibodies.

Some embodiments involve one or more anti-deoxyribonuclease antibodies, for example, anti-DNase 1 antibodies. Some involve antibodies capable of binding to a nonspecific nuclease such as S1 nuclease or micrococcal nuclease. The non-specific nucleases may degrade both RNA and DNA.

In some embodiments, both the first nuclease inhibitor and the second nuclease are anti-nuclease antibodies. Of course, third, fourth, fifth, sixth, and/or more nuclease inhibitors may be used in combination, and all of these may be anti-nuclease antibodies. Some embodiments involve a combination of nuclease inhibitors comprising both antibody inhibitors and non-antibody inhibitors. Many methods will comprise the use of an anti-RNase A antibody. In a preferred embodiment, the anti-RNase A antibody will be an antibody that can bind and inhibit any RNase of the RNase A superfamily, for example, RNase A, RNase B, and RNase C. Some presently preferred embodiments, involve a cocktail comprising at least an anti-RNase A antibody, an anti-RNase 1 antibody, and an anti-RNase T1 antibody.

The first nuclease inhibitor, the second nuclease inhibitor, and/or any other nuclease inhibitors involved in the compositions and methods of the invention may be non-antibody based inhibitors, such as those described elsewhere in the specification. For example, such inhibitors may be is human placental ribonuclease inhibitor, a bovine ribonuclease inhibitor, a porcine ribonuclease inhibitor, diethyl pyrocarbonate, ethanol, formamide, guanidinium thiocyanate, vanadyl-ribonucleoside complexes, macaloid, sodium dodecyl sulfate (SDS), ethylenediamine tetraacetic acid (EDTA), proteinase K, heparin, hydroxylamine-oxygen-cupric ion, bentonite, ammonium sulfate, dithiothreitol (DTT), β-mercaptoethanol, cysteine, dithioerythritol, tris (2-carboxyethyl) phosphene hydrochloride, or a divalent cation such as $Mg^{+2}$, $Mn^{+2}$, $Zn^{+2}$, $Fe^{+2}$, $Ca^{+2}$, or $Cu^+$. Certain embodiments involve the use of human placental ribonuclease inhibitor.

Other embodiments involve solutions comprising at least a first nuclease inhibitor and a second nuclease inhibitor. Such solutions may be "nuclease inhibitor cocktails," "ribonuclease (or RNase) inhibitor cocktails," "deoxyribonuclease (or DNase) inhibitor cocktails," etc., as appropriate based on their activities. Such solutions may comprise a nucleic acid molecule. In some embodiments, the solution is a reagent used in molecular biology, such as described above.

The first and second nuclease inhibitors in such solutions may be any of the anti-nuclease antibodies or non-antibody based inhibitors described above and elsewhere in this specification. In some embodiments, the solution will comprise at least a third anti-nuclease antibody, although any number of such antibodies may be employed. Some presently commercially preferred embodiments comprise at least an anti-RNase A antibody, an anti-RNase 1 antibody, and an anti-RNase T1 antibody, and may further comprise an anti-RNase II antibody, an anti-eosinophil antibody, and an anti-angiogenin antibody. In other preferred embodiments, the solution will comprise at least an anti-DNase 1 antibody, an anti-S1 nuclease antibody, and an anti-micrococcal nuclease antibody. These and other particular embodiments may also comprise human placental ribonuclease inhibitor.

In one presently preferred commercial embodiment, the nuclease inhibitor cocktail is a mixture of anti-ribonuclease antibodies that bind and inactivate RNase A, B and C in addition to RNase 1 and RNase T1.

In some specific embodiments, the invention concerns methods of performing in vitro translation comprising obtaining a first nuclease inhibitor, which inhibitor is further defined as an anti-nuclease antibody, and placing the anti-nuclease antibody in an in vitro translation reaction. In many cases, the in vitro translation reaction comprises at least one nuclease, which may be a ribonuclease, a deoxyribonuclease, or a nonspecific nuclease, as described elsewhere in the specification. Of course, the reaction may further comprise a combination of two or more nucleases. The in vitro translation reaction will also comprise a nucleic acid, which will usually be RNA, in particular, the mRNA to be employed in translation. However, the reaction may also comprise DNA, for example, as the result of a cell-based isolation procedure or a coupled, linked, or separated transcription/translation reaction performed according to any of a number of methods known to those of skill in the art. The anti-nuclease antibody can be any of those described above. In many cases the methods involve obtaining a second nuclease inhibitor and placing the second nuclease inhibitor in the in vitro translation reaction. The second nuclease inhibitor can be any anti-nuclease antibody or non-antibody nuclease inhibitor as described elsewhere in the specification. In some preferred embodiments, the first nuclease inhibitor is an anti-micrococcal nuclease antibody and the second anti-nuclease antibody is an anti-ribonuclease antibody. These methods will often involve the use of cell-free translation systems, such as, for example, the reticulocyte lysate, wheat germ lysate, *Drosophila* lysate, yeast lysate, etc. systems known to those of skill in the art and described in the literature and elsewhere in the specification.

The invention also relates to kits for the performance of various microbiological procedures, which kits comprise the nuclease inhibitors described herein. These kits may contain either a single nuclease inhibitor, or multiple nuclease inhibitors. In some cases, these kits may contain a cocktail of nuclease inhibitors, as described elsewhere in the specification. In one particular embodiment, the kit is further defined as a kit for in vitro translation and comprises at least one anti-nuclease antibody and some or all of the necessary components for, or to make, a cell-free translation system. Such systems are known to those of skill in the art.

DETAILED DESCRIPTION

The methods and compositions of the present invention provide for rapidly inhibiting and/or inactivating nucleases using anti-nuclease antibodies, non-antibody nuclease inhibitors, or both. By employing the methods and compositions of the present invention, a sample of DNA or RNA maintains its intact, full-length form during production and storage.

The Present Invention

The present invention comprises methods and compositions for rapidly inhibiting and/or inactivating nucleases (deoxyribonucleases (DNases) and ribonucleases (RNases)) using at least two nuclease inhibitors. These nuclease inhibitors may be one or more anti-nuclease antibodies, one or more non-antibody nuclease inhibitors, or a combination of at least one anti-nuclease antibody and at least one non-antibody nuclease inhibitor. The non-antibody nuclease inhibitors may be proteinaceous inhibitors, such as Human Placental RNase Inhibitor (RIP), or non-proteinaceous inhibitors, such as divalent cations. Of course, one can determine other nuclease inhibitors by employing the methods disclosed.

In one presently preferred commercial embodiment, the nuclease inhibitor cocktail is a mixture of protein-based ribonuclease inhibitors that non-covalently bind and inactivate RNase A, B and C in addition to RNase 1 and RNase T1. This nuclease inhibitor cocktail is distinct from human placental ribonuclease inhibitor in that it has more robust interaction with RNases and does not release active RNases in the absence of dithiothreitol (DTT) or other reducing agents. It is an antibody-based, RNase-free mixture of different RNase inhibitors which can be useful in solving many RNase contamination problems. The nuclease inhibitor cocktail designed to block RNase A, B, C, RNase T1 and RNase 1 activities may be provided in some embodiments with final concentrations in the cocktail of 25 U/µl (~9 mg/ml) of anti-RNase A, 4.5 mg/ml of anti-RNase 1 and 4.5 mg/ml of anti-RNase T1. However, any concentrations that accomplish the goals of the invention are within the scope of the invention.

The present invention can be employed to inhibit and/or inactivate nucleases, thereby providing reagents that are free of RNase activity and DNase activity. For example, the anti-RNase antibodies of the present invention have a broader spectrum than human placental RNase Inhibitor (RIP), inhibit common eukaryotic and prokaryotic nucleases (RNase A, B, C, RNase 1, T1, etc.), do not interfere with action of SP6, T7, and T3 polymerase, M-MLV Reverse Transcriptase or Taq DNA polymerase, are effective from pH 5.0 to 8.5, and are active from 37° C. to 65° C.

DEFINITIONS

As used herein, the term "inhibition" of nuclease activity means that activity of at least one nuclease is reduced in a sample treated according to the invention relative to a sample not treated according to the invention. "Inhibition" does not require nuclease inactivation or even substantial nuclease inactivation. The term "substantial inhibition" connotes that there is no substantial degradation of DNA or RNA detected in a composition that may contain DNA or RNA. "Substantial" degradation is defined as degradation that would impair the use of the DNA or RNA in the types of protocols described in this specification. As used herein, the terms "nuclease inactivation" or the "inactivation of nucleases" denotes that there is no detectable degradation of the sample DNA or RNA under the assay conditions used, and that the nuclease is irreversibly rendered inoperative. The term "substantially inactivated" connotes that there is no substantial degradation of DNA or RNA detected in a composition that may contain DNA or RNA, and that the nuclease is irreversibly rendered inoperative.

A combination of at least two nuclease inhibitors is referred to herein as a "nuclease inhibitor cocktail." The nuclease inhibitors include anti-nuclease antibodies and non-antibody nuclease inhibitors ("other nuclease inhibitors").

"In vitro translation" is a process of protein synthesis outside the living cell using cell-free extract and mRNA transcript as genetic material for translation. Examples of in vitro translation reactions include IVT Retic Lysate™ or IVT Wheat Germ™ (Ambion). Of course, those of ordinary skill in the art will understand how to perform in vitro translation reactions with other than the examples given.

"In vitro coupled transcription/translation" is a process of protein synthesis in a cell-free lysate where the starting genetic material is DNA and both transcription and translation processes are proceeding simultaneously. An example of in vitro coupled transcription/translation is the PROTEINscript-PRO™ system (Ambion). One of ordinary skill in the art will be able to perform in vitro coupled transcription/translation reactions with other than the example given.

An "in vitro transcription reaction" is the production of RNA from a DNA template under control of specific RNA polymerase(s) in the presence of rNTPs in the transcription buffer optimized for in vitro transcription. Examples of in vitro transcription reaction are MAXIscript™, MEGAscript™, and mMESSAGE mMACHINE™ (Ambion). One of ordinary skill in the art will understand how to perform in vitro transcription reactions with other than the examples given.

In standard in vitro translation reactions, purified RNA is used as a template for translation. "Linked" and "coupled" systems, on the other hand, use DNA as a template. RNA is transcribed from the DNA and subsequently translated without any purification. Such systems typically combine a prokaryotic phage RNA polymerase and promoter (T7, T3, or SP6) with eukaryotic or prokaryotic extracts to synthesize proteins from exogenous DNA templates. DNA templates for transcription:translation reactions may be cloned into plasmid vectors or generated by PCR. The "linked" system is a two-step reaction, based on transcription with a bacteriophage polymerase followed by translation in the rabbit reticulocyte lysate or wheat germ lysate. Because the transcription and translation reactions are separate, each can be optimized to ensure that both are functioning at their full potential.

Unlike eukaryotic systems where transcription and translation occur sequentially, in *E. coli*, transcription and translation occur simultaneously within the cell. In vitro *E. coli* translation systems are thus performed the same way, coupled, in the same tube under the same reaction conditions. During transcription, the 5' end of the RNA becomes available for ribosomal binding and undergoes translation while its 3' end is still being transcribed. This early binding of ribosomes to the RNA maintains transcript stability and promotes efficient translation. This bacterial translation system gives efficient expression of either prokaryotic or eukaryotic gene products in a short amount of time. Use of *E. coli* extract also eliminates cross-reactivity or other problems associated with endogenous proteins in eukaryotic lysates.

Following long-standing patent law, the words "a" and "an," when used in conjunction with the word "comprising" in the claims or specification, denote one or more.

Nucleases

Nucleases are capable of degrading ribonucleic acid (RNA) and/or deoxyribonucleic acid (DNA). The nucleases may specifically degrade RNA or DNA, or may be non-specific nucleases, such as S1 nuclease and micrococcal nuclease, and degrade both RNA and DNA. The nucleases encompassed by the present invention include exonucleases and endonucleases.

Ribonucleases (RNases)

Ribonucleases that are inhibited using the present invention include, but are not limited to, RNase A, RNase B, RNase C, RNase 1, RNase T1, micrococcal nuclease, S1 nuclease, or DNase 1. Additional eukaryotic ribonucleases may be inactivated, such as mammalian ribonuclease 1 family, ribonuclease 2 family, mammalian angiogenins, RNase H family, RNase L, eosinophil RNase, messenger RNA ribonucleases (5'-3' Exoribonucleases, 3'-5' Exoribonucleases), decapping enzymes and deadenylases. Additional ribonucleases that may be inhibited and/or inactivated by the methods and compositions of the present invention include *E. coli* endoribonucleases (RNase P, RNase III, RNase E, RNase I,I*, RNase HI, RNase HII, RNase M, RNase R, RNase IV, F; RNase P2,O, PIV, PC, RNase N), *E. coli* exoribonucleases (RNase II, PNPase, RNase D, RNase BN, RNase T, RNase PH, OligoRNase, RNase R), RNase Sa, RNase F1, RNase U2, RNase Ms, and RNase St. Both endonucleases and exonucleases can be inhibited by the nuclease inhibitor cocktail of the present invention. One of skill in the art can readily employ the methods and compositions of the present invention to inhibit and/or inactivate other RNases known in the art beyond those specifically named herein.

Deoxyribonucleases (DNases)

Deoxyribonucleases that can be inhibited and/or inactivated using the present invention include, but are not limited to, DNase 1, S1 nuclease, and micrococcal nuclease. The nuclease inhibitor cocktail of the present invention can be used to inhibit both endonucleases and exonucleases. One of skill in the art can readily employ the methods and compositions of the present invention to inhibit and/or inactivate other DNases known in the art beyond those specifically named herein.

Compositions

The compositions to which the present methods may be applied in order to inhibit and/or inactivate nucleases will be generally in a liquid form, although a solid composition, such as a matrix comprising immobilized nuclease inhibitor, is also contemplated within the scope of the present invention. If liquid, the composition may be, for example, a reagent used in molecular biology. Representative reagents that may be employed in the present invention include, but are not limited to, water, tris-ethylenediamine tetraacetic acid buffer (TE buffer), sodium chloride/sodium citrate buffer (SSC), 3-(N-morpholinol) propanesulfonic acid (MOPS), Tris buffer, ethylenediamine tetraacetic acid, nucleic acid hybridization buffer, sodium acetate buffer, DNase I digestion buffer, transcription buffer, reverse transcription buffer, cell free extract for in vitro translation, in situ hybridization buffer, and nucleic acid storage buffer/solution. One of skill in the art will understand that the methods of the present invention can be employed with compositions in addition to those named above.

Anti-Nuclease Antibodies

The anti-nuclease antibodies employed in the present invention may be anti-ribonuclease antibodies or anti-deoxyribonuclease antibodies. The anti-ribonuclease antibodies may be antibodies that inhibit one or more of the following ribonucleases: RNase A, RNase B, RNase C, RNase 1, RNase T1, micrococcal nuclease, S1 nuclease, mammalian ribonuclease 1 family, ribonuclease 2 family, mammalian angiogenins, RNase H family, RNase L, eosinophil RNase, messenger RNA ribonucleases (5'-3' Exoribonucleases, 3'-5' Exoribonucleases), decapping enzymes, deadenylases, $E.$ $coli$ endoribonucleases (RNase P, RNase III, RNase E, RNase I,I*, RNase HI, RNase HII, RNase M, RNase R, RNase IV, F; RNase P2,O, PIV, PC, RNase N), $E.$ $coli$ exoribonucleases (RNase II, PNPase, RNase D, RNase BN, RNase T, RNase PH, OligoRNase, RNase R), RNase Sa, RNase F1, RNase U2, RNase Ms, and RNase St. Antibodies to additional RNases not specifically disclosed herein can also be employed in the present invention to inhibit and/or inactivate those RNases, or other RNases.

The anti-nuclease antibodies employed in the present invention may also be anti-deoxyribonuclease antibodies that inhibit one or more of the following deoxyribonucleases: DNase 1, S1 nuclease, and micrococcal nuclease. DNases will often require the presence of cations, such as $Mg^{+2}$ or $Ca^{+2}$. Antibodies to additional DNases not specifically disclosed herein can also be employed in the present invention to inhibit and/or inactivate those DNases.

The anti-nuclease antibodies may be present in a concentration of up to 100 mg/ml, more preferably in a concentration of up to 50 mg/ml, and even more preferably in a concentration of up to 20 mg/ml. In some embodiments the anti-nuclease antibodies will be present in a concentration of 10 to 0.5 mg/ml. In the most preferred embodiment, the concentration of the anti-nuclease antibodies will be 3 to 4 mg/ml.

For some embodiments of the invention, it will be desired to produce antibodies that bind to a particular nuclease. Means for preparing and characterizing antibodies are well known in the art.

Methods for generating polyclonal antibodies are well known in the art, and a specific method for doing so to generate antibodies to RNase is described in the examples below. Generally, a polyclonal antibody is prepared by immunizing an animal with an antigenic composition and collecting antisera from that immunized animal. A wide range of animal species can be used for the production of antisera. Typically the animal used for production of antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobenzoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed $Mycobacterium$ $tuberculosis$), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, may also be given. The process of boosting and titering is repeated until a suitable titer is achieved. When a desired level of immunogenicity is obtained, the immunized animal can be bled and the serum isolated and stored, and/or in some cases the animal can be used to generate monoclonal antibodies (MAbs). For production of rabbit polyclonal antibodies, the animal can be bled through an ear vein or alternatively by cardiac puncture. The removed blood is allowed to coagulate and then centrifuged to separate serum components from whole cells and blood clots. The serum may be used as is for various applications or the desired antibody fraction may be purified by well-known methods, such as affinity chromatography using another antibody or a peptide bound to a solid matrix.

Monoclonal antibodies (MAbs) may be readily prepared through use of well-known techniques. Typically, this technique involves immunizing a suitable animal with a selected immunogen composition, e.g., a purified or partially purified expressed protein, polypeptide or peptide. The immunizing composition is administered in a manner that effectively stimulates antibody producing cells.

The methods for generating monoclonal antibodies (MAbs) generally begin along the same lines as those for preparing polyclonal antibodies. Rodents such as mice and rats are preferred animals, however, the use of rabbit, sheep or frog cells is also possible. Mice are preferred, with the BALB/c mouse being most preferred as this is most routinely used and generally gives a higher percentage of stable fusions.

The animals are injected with antigen as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and have enzyme deficiencies that render them incapable of growing in certain selective media that support the growth of only the desired fused cells (hybridomas).

Any one of a number of myeloma cells may be used, as are known to those of skill in the art. For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus, polyethylene glycol (PEG), such as 37% (v/v) PEG, and other compounds are known in the art. The use of electrically induced fusion methods is also appropriate.

Fusion procedures usually produce viable hybrids at low frequencies, about $1 \times 10^{-6}$ to $1 \times 10^{-8}$. However, this low frequency does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and thus they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

Large amounts of the monoclonal antibodies of the present invention may also be obtained by multiplying hybridoma cells in vivo. Cell clones are injected into mammals that are histocompatible with the parent cells, e.g., syngeneic mice, to cause growth of antibody-producing tumors. Optionally, the animals are primed with a hydrocarbon, especially oils such as pristane (tetramethylpentadecane) prior to injection.

Non-Antibody Nuclease Inhibitors

The invention also envisions the use of non-antibody compounds that function to inhibit nucleases. Suitable such non-antibody nuclease inhibitors include, but are not limited to, diethyl pyrocarbonate, ethanol, formamide, guanidinium thiocyanate, vanadyl-ribonucleoside complexes, macaloid, sodium dodecylsulfate (SDS), ethylenediamine tetraacetic acid (EDTA), proteinase K, heparin, hydroxylamine-oxygen-cupric ion, bentonite, ammonium sulfate, dithiothreitol (DTT), β-mercaptoethanol, cysteine, dithioerythritol, urea, polyamines (spermidine, spermine), detergents (sodium dodecylsulfate, NP 40, Tween 20, Triton X-100), tris (2-carboxyethyl) phosphene hydrochloride (TCEP), and divalent cations ($Mg^{+2}$, $Mn^{+2}$, $Zn^{+2}$, $Fe^{+2}$, $Ca^{+2}$, $Cu^{+2}$). Using the information provided in this specification, one of skill in the art will be able to identify additional compounds that may be employed in practicing the present invention.

Non-ionic detergents (NP 40, Tween 20, Triton X-100) are not inhibitory of nucleases per se, but have a synergistic effect with anti-nuclease antibodies to enhance the activity of the anti-nuclease antibodies.

Anti-Nuclease Cocktail

As indicated above, the nuclease inhibitor cocktail of the present invention comprises a combination of at least two nuclease inhibitors. Preferably, the nuclease inhibitor cocktail of the present invention remains active over a broad range of conditions. In a preferred embodiment, the nuclease inhibitor cocktail is active in the presence or absence of DTT. In the most preferred embodiment, DTT can be added up to 200 mM without affecting the activity of anti-nuclease antibodies in the cocktail. A preferred embodiment can be used in a broad functional temperature range, including from 4° C. to 65° C., and at a pH of from 5.5 to 8.5. A preferred embodiment will remain effective at inhibiting nucleases in the presence of guanidinium thiocyanate up to 3 M, and of urea up to 6 M.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Criteria for the Analysis of Nuclease Inactivation

The inventors routinely perform assays on RNA and DNA designed to assess RNase and DNase activity in a sample. Many assays may be used for the detection of nuclease activity, including non-isotopic and isotopic assays. The isotopic assay is described below. The assays generate similar data with regard to the sensitivity of detection.

In such assays, the inactivation process is typically performed on a mixture of three different ribonucleases: RNase A, RNase 1, and RNase T1. Each ribonuclease may be purified from a different species: human, *E. coli* and fungal, respectively. The three RNases are very different from each other in their origin, substrate specificity, and protein sequence. In this way, the inactivation process can test three completely different but well characterized ribonucleases.

By employing assays, one of skill will be able to determine additional anti-nuclease antibodies that function in the invention. In order to do so, one need only obtain a putative antibody that is expected to have nuclease inactivating activity and then perform the types of assays performed herein to determine the utility of the putative antibody in the methods and compositions of the invention.

The isotopic RNase assay uses a radioactive RNA synthesized by in vitro transcription of the RNA substrate. The radioactive RNA is synthesized using a T7 MAXIscript™ transcription kit (Ambion, Inc.). The in vitro transcription reaction mixture may contain, for example, 1.0 μg of linearized DNA template, 2 μl of 10× transcription buffer, 0.02 μl of UTP[$\alpha$-$^{32}$P] (800 Ci/mmol), 2 μl of each 10 mM ribonucleotide, and 2 μl of the T7 RNA polymerase mix, with a final volume of 20 μl. The reaction is incubated at 37° C. for 30 min. The transcript is purified by phenol:chloroform extraction and used directly for RNase inactivation assay ($2.2 \times 10^5$ counts per minute (approximate specific activity of the probe)/2.3 ng RNA).

Two μl of the RNA probe are incubated with the test sample in a final volume of 10 μl for about 16 hours at 37° C. After incubation, the RNA is fractionated in a denaturing 6 M urea 5% acrylamide gel. The gel is then exposed to x-ray film. Untreated RNA is also fractionated as a control with the test samples for comparative purposes. Test samples containing no detectable RNase activity produce the same single band as the untreated control RNA. RNase activity is indicated by the intensity of the RNA decreasing and by the appearance of smearing below the intact RNA.

One of skill in the art can employ the same type of method disclosed above, appropriately adapted, to assay for inactivation of DNase. For example, assays for analysis of the DNA degrading activities of nuclease S1, Micrococcal nuclease, and DNase 1 are disclosed in Example 4.

Example 2

Preparation and Isolation of Anti-Nuclease Antibodies

Anti-nuclease antibodies are generated by injecting rabbits with, for example, purified antigens RNase A, RNase T1, RNase 1, Micrococcal nuclease, or S1 nuclease mixed with complete or incomplete Freund's adjuvant. Complete adjuvant (0.5 ml) is mixed with 0.5 ml of antigen solution containing 100 μg of antigen in PBS buffer, and drawn into a syringe with an attached 19-G needle. For the first immunization, 100 μg of the antigen in 0.5 ml of complete adjuvant is injected into each rabbit; 250 μl is injected deeply into each thigh muscle and into each of two sites through the skin on the shoulders. Injections are then repeated biweekly for four weeks using incomplete adjuvant.

Ten days after the final injection, a sample of the rabbit's blood for testing is collected from the marginal ear vein into a sterile glass universal container. The collected blood is allowed to clot by letting it stand at room temperature for 2 hours and then at 4° C. overnight. The serum is separated from the blood by detaching the clot carefully with a spatula from the walls of the container and pouring the liquid into a centrifuge tube. The clot is then centrifuged at 2500 g for 30 min at 4° C., and any expressed liquid is removed. This liquid is added to the clot-free liquid collected previously and the pooled liquid is centrifuged as described above. The serum is removed from the cell pellet with the Pasteur pipet. The serum is tested for the presence of antibodies by ELISA (see below). If the antibody reaction is weak, the rabbit is injected again one month after the test with 100 μg of antigen. Blood is drawn again ten days after this injection. To keep the antibody titers high, the rabbi is injected every month. Blood is drawn for antibody testing ten days after each injection. Antibodies are stored in small aliquots at a minimum of −20 C.

An ELISA test is used to determine antibody titer in the immunized sera. In this test, the wells of a standard assay plate (96 well plate, VWR, cat. #62409-050) are coated with purified antigen (Ambion: RNase A (cat. #2271), RNase 1 (cat. #2294), RNase T1 (cat. #2280). Ten wells are required for each serum tested, and it is possible to use assay plates with 9 or 12 well strips, or use only a portion of a standard 96 well plate. Antigen is diluted to 0.25 μg/ml in 1×PBS buffer (Ambion, cat. #9625), and 100 μl of the diluted antigen is added to each well. The plate is incubated for a minimum of 2 hours at room temperature, or overnight at 4° C. After incubation, each well is washed at least three times with double distilled $H_2O$ and the wells are tapped dry. The unbound sites in the well plate are blocked by adding 100 μl blocking buffer (1% BSA in PBS) (10×PBS, Ambion cat. #9625; BSA, Ambion, cat. # 2616) to each well and shaking 60 minutes at room temperature. Each well is then washed at least three times with double distilled $H_2O$ and tapped dry. In order to add primary antibody, the antisera is diluted 500× in blocking buffer and serially diluted across the row of the well plate as follows: blank, secondary antibody only (2000× dilution in blocking buffer), primary antibody only (500×), 500×, 1000×, 2000×, 4000×, 8000×, and 16000×.

100 μl of 500× is added to well 3 and 200 μl is added to well 4. 100 μl blocking buffer is added to wells 1,2, and 5–10. 100 μl is taken from well 4 and added to well 5. The contents of the wells are mixed thoroughly by pipeting up and down. 100 μl is removed from well 5 and mixed into well 6. Dilution is continue in this manner across the row. The well plate is then incubated for two hours at room temperature with gentle shaking. Each well is then washed at least three times with double distilled $H_2O$ and tapped dry.

The secondary goat-anti-rabbit-HRP antibody (Zymed, cat. #65-6120) is diluted 2000× in blocking buffer. 100 μl is added to wells 2, and 4–10. The wells are incubated 60 minutes at room temperature with gentle shaking. Then each well is washed at least three times with double distilled $H_2O$ and tapped dry.

100 μl ABTS color development solution (Zymed, cat. #00-2024) is added to each well, and the wells are incubated for 20 minutes at room temperature. 25 μl 2M $H_2SO_4$ (J. A. Baker, cat. #g6781-05) is then added to each well to stop the reaction.

Absorbance is read at 405 nm in a plate reader. The first 3 wells (controls) should be negative (i.e., no color) to verify that none of the components generated false positive results. An acceptable titer will give strong signal ($A_{405}$>1) with the 1000× dilution of sera. A good titer will give strong signal with 4000× and higher.

Example 3

Anti-Nuclease Antibody Purification Procedure

Anti-nuclease antibodies employed in the invention may be purified. For example, 500 ml of anti-RNase A serum or 300 ml of anti-RNase T1 or 1 serum is thawed in a 37° C. water bath and combined into one flask. Then 45% ammonium sulfate (2.77 g solid $(NH_4)_2SO_4$ for 10 ml solution) (USB, cat. #112544) is slowly added to the serum with stirring at 4° C., avoiding any local saturation in the serum, in order to precipitate the globulins. The solution is stirred for an additional two hours at 4° C. The solution is added to 50 ml centrifuge tubes and spun at 14,000 rpm for 15 minutes to pellet the protein. The supernatant is removed and the pellet is dissolved in 50 mM sodium borate (pH 9.0). The dissolved pellet is dialyzed against three liters of 50 mM sodium borate (pH 9.0) overnight at 4° C.

Next, Triton X-100 is added to the solution to 0.1% and the pH is adjusted to 9.0 using sodium hydroxide (NaOH). The solution is stirred for 30 minutes at 4° C. The solution is then loaded onto a 25 ml Protein A Sepharose column (Protein A Sepharose, Pharmacia, cat. #17-0963-03) equilibrated with 50 mM sodium borate (pH 9.0) and 0.1% Triton. The column is washed with three column volumes of 50 mM sodium borate and 0.1% Triton. The column is then washed with two column volumes of the same buffer plus 3 M lithium chloride (LiCl). The pH of the solution should be adjusted to 9.0 after addition of the LiCl. Then wash the column with three column volumes of 50 mM sodium borate without Triton to remove the remaining detergent.

The protein is eluted with 100 mM glycine (pH 3.0) (Ultrapure Glycine, Gibco-BRL, cat. #15514-029). A fresh tube is used when the protein begins to elute from the column. Eight ml fractions of protein is eluted into 400 μl of 1 M potassium phosphate buffer (pH 7.7). Each tube is inverted several times to mix the buffer after each fraction is finished to prevent denaturing of the enzyme. A new tube is used when the protein is finished eluting to prevent dilution of the protein.

The fractions are pooled and the pH is adjusted to 6.0 with dilute HCl. The pooled fractions are loaded onto a 5 ml SP sepharose column (SP-Sepharose, Pharmacia cat. #17-0729-01) equilibrated with 20 mM potassium phosphate buffer (pH 6.8). The antibody will come off in the flowthrough fractions. The tubes are fed to a new fraction once the protein begins to flow through. The antibody fractions are dialyzed against three liters of 20 mM potassium phosphate buffer (pH 7.7), overnight at 4° C. with stirring.

The antibodies are loaded onto a 5 ml DEAE AffiBlue Gel column (DEAE AffiBlue, BioRad cat. #153-7307) equilibrated with 20 mM potassium phosphate buffer (pH 7.7). The antibodies will come off into the flowthrough fractions. The pH of the antibody fraction is adjusted to 6.0 with dilute HCl. The solution is then loaded onto an 8 ml denatured DNA column (Denatured DNA-cellulose, Pharmacia cat. #27-5579-$O_2$) equilibrated with 20 mM potassium phosphate buffer (pH 6.8). The antibodies come off in a sharp peak in the flowthrough material. The antibody fractions are pooled. The pH of anti-RNase A is adjusted to 7.7. Conductivity should be equal to 20 mM potassium phosphate buffer (pH 7.7)+10 mM NaCl. The antibodies may be diluted if necessary.

Anti-RNase A is loaded onto a 50 ml Q-sepharose column (Q-Sepharose Fast Flow, Pharmacia cat. #17-0510-01) equilibrated with 20 mM potassium phosphate buffer (pH 7.7) plus 10 mM NaCl plus 10% glycerol. The column is washed with 5 column volumes of the equilibrating buffer. The protein is then eluted with 20 mM potassium phosphate buffer (pH 7.7) and 10% glycerol.

One of skill in the art will be able to employ the disclosed method, appropriately adapted, to purify anti-DNase antibodies and non-specific anti-nuclease antibodies.

Example 4

Activity Assays for Anti-Nuclease Antibodies

The activity of anti-nuclease antibodies is readily determined using radiolabeled RNA or DNA to detect the inhibition of RNase or DNase by the anti-nuclease antibodies. In general, the nuclease and anti-nuclease antibody are separately diluted, typically in 1× assay buffer. Assay buffer, nuclease and anti-nuclease antibody are then added to 0.5 ml microfuge tubes. For assaying anti-RNase activity, a mixture comprising assay buffer, RNA and radiolabeled RNA is added to the microfuge tubes. The "MIX" of assay buffer, RNA and radiolabeled RNA is generally prepared by combining 10× Assay Buffer (0.9 µl/rxn), 5 mg/ml yeast RNA (0.4 µl/rxn), $^{32}$P-β actin RNA ($_1$ µl/rxn), and nuclease-free H$_2$O (6.7 µl/rxn) for a total of 9 µl/rxn. The tubes are vortexed and microfuged, then incubated at 37° C. for 30 minutes. After incubation, a portion of the tube contents is removed and placed into gel loading buffer. Then the tube contents and the gel loading buffer are mixed, and the combination is loaded onto a gel, typically a 8M urea/5% acrylamide gel, which is exposed to film.

Components typically employed in these activity assays include:

10× Assay Buffer (200 mM Tris-HCl pH 7.5, 500 mM NaCl, 10 mM EDTA)
1× Assay Buffer (20 mM Tris-HCl pH 7.5, 50 mM NaCl, 1 mM EDTA, 0.1 mg/ml BSA)
BSA, 50 mg/ml (Ambion cat. #2616)
Medium specific-activity $^{32}$P-labeled β-actin RNA probe
5 mg/ml yeast total RNA (Ambion cat. #7120G)
nuclease-free H$_2$O
Gel Loading Buffer II (Ambion cat. #8546G)
8M urea/5% acrylamide gel
Tris-borate/EDTA (TBE buffer)

The above method has been used by the inventors for activity assays of numerous anti-nuclease antibodies. Examples follow.

1. Activity Assay for Anti-RNase A

Radiolabeled RNA was used to detect the inhibition of RNase A by specific antibodies. The assay followed the method disclosed above. In particular, RNase A (1 mg/ml) was diluted to 25 pg/µl in 1× Assay Buffer and Anti-RNase A was diluted to 25 U/µl. The "MIX" of assay buffer, RNA and radiolabeled RNA was prepared as disclosed above. The reactions were set up in 0.5 ml microfuge tubes as indicated in the table below. 1× Assay Buffer was added first, then the nuclease and Anti-RNase A were added, with MIX added as a last component. The tubes were vortexed and microfuged, then incubated at 37° C. for 30 min.

| Tube | 1X Assay Buffer (µl) | RNase A (µl) | Anti-RNase A Antibody (µl) | MIX (µl) |
|---|---|---|---|---|
| 1 | 11 | — | — | 9 |
| 2 | 10 | 1 (25 pg) | — | 9 |
| 3 | 9 | 2 (50 pg) | — | 9 |
| 4 | 8 | 3 (75 pg) | — | 9 |
| 5 | 7 | 4 (100 pg) | — | 9 |
| 6 | 10 | — | 1 | 9 |
| 7 | 9 | 1 | 1 | 9 |
| 8 | 8 | 2 | 1 | 9 |
| 9 | 7 | 3 | 1 | 9 |
| 10 | 6 | 4 | 1 | 9 |
| 11 | 11 | — | — | 9 |

At the end of the incubation time, 10 µl of solution was removed from the tube and placed into 10 µl Gel Loading Buffer II. The combination was mixed thoroughly and loaded onto a 8M urea/5% acrylamide gel. The gel was exposed to film for 30 min. at −80° C. with an intensifying screen.

The probe should be completely degraded with all levels of RNase A alone. There should be a full-length probe visible in the presence of 50 pg RNase A and a final concentration of 1 U/µl Anti-RNase A.

2. Activity Assay for Anti-RNase 1

Radiolabeled RNA was used to detect the inhibition of RNase 1 by specific antibodies. The assay followed the method disclosed above. In particular, RNase 1 (100 U/µl) was diluted to 1 U/µl in 1× Assay Buffer. The "MIX" was prepared as disclosed above. The reactions were set up in 0.5 ml microfuge tubes as indicated in the table below. 1× Assay. Buffer was added first, then the nuclease, Anti-RNase 1, and MIX were added. The tubes were vortexed and microfuged, then incubated at 37° C. for 30 min.

| Tube | 1X Assay Buffer (µl) | RNase 1 (µl) | Anti-Rnase 1 Antibody (µl) | MIX (µl) |
|---|---|---|---|---|
| 1 | 11 | — | — | 9 |
| 2 | 10 | 1 (1 U) | — | 9 |
| 3 | 8.5 | 2.5 (2.5 U) | — | 9 |
| 4 | 6 | 5 (5 U) | — | 9 |
| 5 | 3.5 | 7.5 (7.5 U) | — | 9 |
| 6 | 10 | — | 1 | 9 |
| 7 | 9 | 1 (1 U) | 1 | 9 |
| 8 | 7.5 | 2.5 (2.5 U) | 1 | 9 |
| 9 | 5 | 5 (5 U) | 1 | 9 |
| 10 | 2.5 | 7.5 (7.5 U) | 1 | 9 |
| 11 | 11 | — | — | 9 |

At the end of the incubation time, 10 µl of solution was removed from the tube and placed into 10 µl Gel Loading Buffer II. The combination was mixed thoroughly and loaded onto a 8M urea/5% acrylamide gel. The gel was exposed to film for 30 min. at −80° C. with an intensifying screen.

The probe should be completely degraded in the presence of RNase 1 alone. There should be a full-length probe visible in the presence of 5U RNase 1 and a final concentration of 0.175 mg/ml anti-RNase 1.

3. Activity Assay for Anti-RNase T1

Radiolabeled RNA was used to detect the inhibition of RNase T1 by specific antibodies. The assay followed the method disclosed above. In particular, RNase T1 (1000 U/µl) is diluted to 0.1 U/µl in 1× Assay Buffer. The "MIX" was prepared as disclosed above. The reactions were set up in 0.5 ml microfuge tubes as indicated in the table below. 1× Assay Buffer was added first, then the nuclease, Anti-RNase T1 (4.5 mg/ml), and MIX ere added. The tubes were vortexed and microfuged, then incubated at 37° C. for 30 min.

| Tube | 1X Assay Buffer (μl) | RNase 1 (μl) | Anti-Rnase T1 Antibody (μl) | MIX (μl) |
|---|---|---|---|---|
| 1 | 11 | — | — | 9 |
| 2 | 10 | 1 (0.1 U) | — | 9 |
| 3 | 9 | 2 (0.2 U) | — | 9 |
| 4 | 8 | 3 (0.3 U) | — | 9 |
| 5 | 6 | 5 (0.5 U) | — | 9 |
| 6 | 10 | — | 1 | 9 |
| 7 | 9 | 1 (0.1 U) | 1 | 9 |
| 8 | 8 | 2 (0.2 U) | 1 | 9 |
| 9 | 7 | 3 (0.3 U) | 1 | 9 |
| 10 | 5 | 5 (0.5 U) | 1 | 9 |
| 11 | 11 | — | — | 9 |

At the end of the incubation time, 10 μl of solution was removed from the tube and placed into 10 μl Gel Loading Buffer II. The combination was mixed thoroughly and loaded onto a 8M urea/5% acrylamide gel. The gel was exposed to film for 30 min. at −80° C. with an intensifying screen.

There should be a full-length probe visible in the presence of 0.3 U RNase T1 and a final concentration of 0.175 mg/ml Anti-RNase T1.

4. Activity Assay for Anti-S1 Nuclease

Radiolabeled RNA or radiolabeled single stranded DNA was used to detect the inhibition of S1 nuclease by specific antibodies. The assay generally followed the method disclosed above. In addition to the components typically used, this assay required both a medium specific activity, $^{32}$P-labeled β-actin RNA probe, and a medium specific activity, $^{32}$P-labeled single-stranded DNA probe. In particular, Nuclease S1 (430 U/μl) was diluted to 0.5 U/μl in 1× Assay Buffer containing 1 mM ZnSO$_4$. The "MIX" was prepared as disclosed above, except that either $^{32}$P-labeled β actin RNA (1 μl/rxn) or $^{32}$P-labeled β actin cDNA (1 μl/rxn) was used. The reactions were set up in 0.5 ml microfuge tubes as indicated in the table below. 1× Assay Buffer was added first, then the nuclease and Anti-nuclease S1 (2–3 mg/ml) were added. The MIX containing radiolabeled substrate was added as a last component. The tubes were vortexed and microfuged, then incubated at 37° C. for 30 min.

| Tube | 1X Assay Buffer (μl) | S1 nuclease (μl) | Anti-S1 nuclease Antibody (μl) | MIX (μl) |
|---|---|---|---|---|
| 1 | 11 | — | — | 9 |
| 2 | 10 | 1 (0.5 U) | — | 9 |
| 3 | 9 | 2 (1 U) | — | 9 |
| 4 | 7 | 4 (2 U) | — | 9 |
| 5 | 3 | 8 (4 U) | — | 9 |
| 6 | 10 | — | 1 | 9 |
| 7 | 9 | 1 (0.5 U) | 1 | 9 |
| 8 | 8 | 2 (1 U) | 1 | 9 |
| 9 | 6 | 4 (2 U) | 1 | 9 |
| 10 | 4 | 8 (4 U) | 1 | 9 |

At the end of the incubation time, 10 μl of solution was removed from the tube and placed into 10 μl Gel Loading Buffer II. The combination was mixed thoroughly and loaded onto a 8M urea/5% acrylamide gel. The gel was exposed to film for 30 min. at −80° C. with an intensifying screen.

The RNA or DNA probe should be completely degraded in the presence of S1 nuclease alone. There should be a full-length probe visible in the presence of 1 U S1 nuclease and a final concentration of 0.2 mg/ml Anti-S1 antibodies.

5. Activity Assay for Micrococcal Nuclease

Radiolabeled RNA or radiolabeled single stranded cDNA was used to detect the inhibition of Micrococcal nuclease by specific antibodies. The assay generally followed the method disclosed above. In addition to the components typically used, this assay required both a medium specific activity, $^{32}$P-labeled β actin RNA probe, and a medium specific activity, $^{32}$P-labeled single-stranded DNA probe. In particular, Micrococcal nuclease (15 U/μl) was diluted to 1 U/μl in 1× Assay Buffer containing 1 mM CaCl$_2$. The "MIX" was prepared as disclosed above, except that either $^{32}$P-labled β actin RNA (1 μl/rxn) or $^{32}$P-labeled β actin cDNA (1 μl/rxn) was used. The reactions were set up in 0.5 ml microfuge tubes as indicated in the table below. 1× Assay Buffer was added first, then the nuclease and Anti-nuclease (2–3 mg/ml) were added. The MIX containing radiolabeled substrate was added as a last component. The tubes were vortexed and microfuged, the incubated at 37° C. for 30 min.

| Tube | 1X Assay Buffer (μl) | Micrococcal nuclease (μl) | Anti-Micrococcal-nuclease Antibody (μl) | MIX (μl) |
|---|---|---|---|---|
| 1 | 11 | — | — | 9 |
| 2 | 10 | 1 (0.5 U) | — | 9 |
| 3 | 9 | 2 (1 U) | — | 9 |
| 4 | 7 | 4 (2 U) | — | 9 |
| 5 | 3 | 8 (4 U) | — | 9 |
| 6 | 10 | — | 1 | 9 |
| 7 | 9 | 1 (0.5 U) | 1 | 9 |
| 8 | 8 | 2 (1 U) | 1 | 9 |
| 9 | 6 | 4 (2 U) | 1 | 9 |
| 10 | 4 | 8 (4 U) | 1 | 9 |

At the end of the incubation time, 10 μl of solution was removed from the tube and placed into 10 μl Gel Loading Buffer II. The combination was mixed thoroughly and loaded onto a 8M urea/5% acrylamide gel. The gel was exposed to film for 30 min. at −80°C. with an intensifying screen.

The RNA or DNA probe should be completely degraded in the presence of S1 nuclease alone. There should be a full-length probe visible in the presence of 1 U Micrococcal nuclease and a final concentration of 0.2 mg/ml Anti-micrococcal antibodies.

6. Activity Assay for Anti-DNase 1

Radiolabeled single stranded DNA was used to detect the inhibition of DNase 1 by specific antibodies. The assay generally followed the method disclosed above, with certain exceptions indicated below.

Components employed in this activity assay include:
10× Assay Buffer (200 mM Tris-HCl pH 7.8, 500 mM NaCl, 50 mM MgCl$_2$, 50 mM CaCl$_2$, 10 mM EDTA)
  (This 10× assay buffer differs from that used in the general method in the addition of 50 mM MgCl$_2$ and 50 mM CaCl$_2$, and in having a pH of 7.8)
1× Assay Buffer (20 mM Tris-HCl pH 7.5, 50 mM NaCl, 5 mM MgCl$_2$, 5 mM CaCl$_2$, 1 mM EDTA, 0.1 mg/ml BSA)
  (This 1× assay buffer differs from that used in the general method in the addition of 5 mM MgCl$_2$ and 5 mM CaCl$_2$.)
BSA, 50 mg/ml (Ambion cat. #2616)
Medium specific-activity β-actin cDNA probe
  (This probe differs from the Medium specific-activity β-actin probe used in the general method.)

nuclease-free H₂O
Gel Loading Buffer II (Ambion cat. #8546G)
8M urea/5% acrylamide gel
TBE buffer DNase 1 was diluted to 1 U/μl in 1× Assay Buffer. The "MIX" was prepared by combining 10× Assay Buffer (0.9 μl/rxn), $^{32}$P-labeled β actin cDNA (1 μl/rxn), and nuclease-free H₂O (7.7 μl/rxn) for a total of 9 μl/rxn. (Note that, unlike in the general method, no yeast RNA was used in the MIX in this sub-example.) The reactions were set up in 0.5 ml microfuge tubes as indicated in the table below. 1× Assay Buffer was added first, then the nuclease and specific anti-nuclease antibody were added. The MIX containing radio-labeled substrate was added as a last component. The tubes were vortexed and microfuged, then incubated at 37° C. for 30 min.

| Tube | 1X Assay Buffer (μl) | DNase 1 (μl) | Anti-DNase 1 Antibody (μl) | MIX (μl) |
|---|---|---|---|---|
| 1 | 11 | — | — | 9 |
| 2 | 10 | 1 (1 U) | — | 9 |
| 3 | 9 | 2 (2 U) | — | 9 |
| 4 | 9 | 1 (1 U) | 1 | 9 |
| 5 | 8 | 2 (2 U) | 1 | 9 |
| 6 | 10 | — | 1 | 9 |
| 7 | 9 | — | 1 | 9 |

At the end of the incubation time, 10 μl of solution was removed from the tube and placed into 10 μl Gel Loading Buffer II. The combination was mixed thoroughly and loaded onto a 8M urea/5% acrylamide gel. The gel was exposed to film for 30 min. at −80° C. with an intensifying screen.

The DNA probe should be completely degraded in the presence of DNase 1 alone. There should be a full-length probe visible in the presence of 2 U DNase 1 and a final concentration of 0.2 mg/ml Anti-DNase 1 antibodies.

Example 5

Activity Assay for an Anti-Nuclease Cocktail

The activity of an anti-nuclease cocktail is readily determined using radiolabeled RNA or DNA to detect the inhibition of nuclease by anti-nuclease antibodies in the anti-nuclease cocktail. In general, the nuclease and anti-nuclease antibodies are separately diluted, typically in 1× assay buffer. Assay buffer, nuclease and an anti-nuclease cocktail are then added to 0.5 ml microfuge tubes. A mixture comprising assay buffer, RNA or DNA and radiolabeled RNA or DNA is added to the microfuge tubes, and the tubes are vortexed and microfuged. After incubation of the tubes at 37° C. for 30 minutes, a portion of the tube contents is removed and placed into gel loading buffer. After mixing, the combination is loaded onto a gel, typically a 8M urea/5% acrylamide gel, which is exposed to film.

The above method has been used by the inventors for activity assays of a specific anti-RNase cocktail as follows:

Radiolabeled RNA was used to detect the inhibition of RNase A, RNase T1, and RNase 1 by specific antibodies. The following components were needed for this assay:

10× Assay Buffer (200 mM Tris-HCl pH 7.5, 500 mM NaCl, 10 mM EDTA)
1× Assay Buffer (20 mM Tris-HCl pH 7.5, 50 mM NaCl, 1 mM EDTA, 0.1 mg/ml BSA)
BSA (50 mg/ml) (Ambion cat. #2616)
Medium specific-activity α-actin probe (QC SOP 0006)
5 mg/ml yeast RNA (Ambion cat. #7120G)
nuclease-free H₂O
Gel Loading Buffer II (Ambion cat. #8546G)
8M urea/5% acrylamide gel
TBE buffer
Specific Anti-RNase Cocktail (25 U/μl Anti-RNase A, 4.5 mg/ml Anti-RNase 1 and 4.5 mg/ml Anti-RNase T1)
Specific RNase Cocktail (RNase A (25 ng/μl), RNase T1 (0.1 U/μl), and RNase I (1 U/μl) in 1× Assay Buffer).

The "MIX" was prepared by combining 10× Assay Buffer (0.9 μl/rxn), 5 mg/ml yeast RNA (0.4 μl/rxn), $^{32}$P-labeled β actin RNA (1 μl/rxn), and nuclease-free H₂O (6.7 μl/rxn), for a total of 9 μl/rxn.

The reactions were set up in 0.5 ml microfuge tubes as indicated in the table below. 1× Assay Buffer was added first. Then Specific RNase Cocktail, Specific Anti-RNase Cocktail and MIX were added. The tubes are vortexed and microfuged, then incubated at 37° C. for 30 min.

| Tube | 1X Assay Buffer (μl) | RNase A (μl) | RNase 1 (μl) | RNase T1 (μl) | Specific Anti-RNase Cocktail (μl) | Mix (μl) |
|---|---|---|---|---|---|---|
| 1 | 11 | — | — | — | — | 9 |
| 2 | 10 | 1 | — | — | — | 9 |
| 3 | 9 | 1 | — | — | 1 | 9 |
| 4 | 9.5 | — | 1.5 | — | — | 9 |
| 5 | 8.5 | — | 1.5 | — | 1 | 9 |
| 6 | 9.5 | — | — | 1.5 | — | 9 |
| 7 | 8.5 | — | — | 1.5 | 1 | 9 |
| 8 | 10 | — | — | — | 1 | 9 |
| 9 | 11 | — | — | — | — | 9 |

At the end of the incubation time, 10 μl of solution was removed from the tube and placed into 10 μl Gel Loading Buffer II. The combination was mixed thoroughly and loaded onto a 8M urea/5% acrylamide gel. The gel was exposed to film for 30 min. at −80° C. with an intensifying screen.

The probe should be fully degraded in the presence of Specific RNase alone, and in the presence of the Specific Anti-RNase Cocktail, there should be full-length probe visible.

Example 6

Non-Antibody Nuclease Inhibitors Tested Alone and in Combination with an Anti-Nuclease Antibody Certain compounds function to inhibit nucleases ("non-antibody nuclease inhibitors"). Such compounds include, but are not limited to, dithiothreitol (DTT), heparin, polyamines (spermidine, spermine), urea, guanidine thiocyanate, detergents (sodium dodecyl sulfate), and divalent cations ($Mg^{+2}$, $Zn^{+2}$, $Cu^{+2}$, $Fe^{+2}$, $Ca^{+2}$). Non-ionic detergents are not inhibitory of nucleases per se, but have a synergistic effect with anti-nuclease antibodies to enhance the activity of the anti-nuclease antibodies.

The action of certain non-antibody nuclease inhibitors was tested by performing assays using an anti-nuclease antibody with and without addition of a non-antibody nuclease inhibitor. Results of these assays indicated inhibition of nuclease activity by the non-antibody nuclease inhibitors, as shown below.

The activities of RNase A, 1 and T1 were assayed in the manner described in Example 5 above, with the exception that $^{32}$P-labeled β actin RNA was incubated with Specific Anti-RNase Cocktail (25 U/μl Anti-RNase A, 4.5 mg/ml Anti-RNase 1 and 4.5 mg/ml Anti-RNase T1) in the absence and presence of non-antibody nuclease inhibitors. The results of these assays were as follows:

| NON-ANTIBODY RNase INHIBITOR | ANTI-RNase ANTIBODY | RESULTS |
| --- | --- | --- |
| DTT | *E. coli* RNase 1 | 1–3 mM DTT inhibited 1 U RNase 1 during 30 minute incubation at 37° C. |
| DTT | RNase T1 | 5–10 mM DTT inhibited 0.15 U RNase T1 |
| DTT | RNase A | At 37° C., DTT up to 250 mM did not inhibit RNase A activity.<br>*DTT mixed with anti-RNase 1 and anti-RNase T1 antibodies enhanced their protective effect against RNases 1 and T1. |
| heparin | *E. coli* RNases 1 | 2.5 to 5 μg of heparin completely inactivated 1 U *E. coli* RNases 1.<br>*This amount of heparin did not effect the activities of RNases A and RNases T1. |
| Polyamines (spermidine, spermine) | RNase A | 5 to 7 mM spermidine inhibited 50 pg of RNase A. |
| Polyamines (spermidine, spermine) | RNase T1 and RNase 1 | 2.5 to 5 mM spermidine inhibited 0.2 U RNase T1 and 2 U RNase 1. |
| Polyamines (spermidine, spermine) | RNase A, T1 and 1 | 5 mM spermidine mixed with Specific Anti-RNase Cocktail enhanced anti-RNase A, 1, and T1 activity of Specific Anti-RNase cocktail. |
| Detergents: SDS | RNase A | 0.25% SDS inhibited activity of 50 pg of RNase A. |
| Detergents: SDS | RNase A, 1, and T1 | Addition of 0.1–0.5% SDS to Specific Anti-RNase Cocktail strengthened anti-RNase A, 1, and T1 action of Specific Anti-RNase Cocktail. |
| Detergents: Triton X-100, NP 40, Tween 20, Chaps | RNase A, 1, and T1 | Common non-ionic (Triton X-100, Tween 20, NP-40) or zwitterionic (CHAPS) detergents, added to Specific Anti-RNase Cocktail in concentrations of 0.1% to 1% strengthened the action of Specific Anti-RNase Cocktail against RNase A, 1, and T1. |
| Detergents: urea | RNase A | 6 M urea inhibited RNase A activity. This concentration of urea added to the Specific Anti-RNase Cocktail strengthened the action of Specific Anti-RNase Cocktail. |
| Detergents: guanidine thiocyanate | | 2–3 M guanidine thiocyanate added to the Specific Anti-RNase Cocktail made it more inhibitory against different antibodies. |
| Detergents: salts - MgCl$_2$ | RNase A, 1, and T1 | 50 to 100 mM MgCl$_2$ was strongly inhibitory for RNase A, 1, and T1 activities. The best results were observed when MgCl$_2$ was mixed together with Specific Anti-RNase Cocktail. |

Those of ordinary skill in the art will be able to determine ranges at which the non-antibody nuclease inhibitors will be active.

Example 11

Nuclease Inhibitor Cocktail Use in In Vitro Transcription Reactions

In vitro synthesis of RNA transcripts from DNA templates uses purified RNA polymerases (SP6, T7 and T3 phage RNA polymerases are widely used). A typical transcription reaction may contain: 10× Transcription Buffer, nucleotides (ATP, CTP, GTP, UTP), DNA template, and RNA polymerase, although modifications will be known to those of skill in the art. RNA produced by these methods can be protected by the nuclease inhibitor cocktail of the present invention. Examples of transcription buffers containing a nuclease inhibitor cocktail are MAXIscript™, MEGAscript™, and mMESSAGE mMACHINE™ (Ambion).

Example 12

Nuclease Inhibitor Cocktail Use in Reverse Transcription Reaction

The nuclease inhibitor cocktail may be used to prevent degradation of RNA in reverse transcription reactions where reverse transcriptase is used to copy an RNA target into its complementary DNA sequence (cDNA). The cDNA can then be amplified exponentially via PCR™. A typical reverse transcription reaction and amplification reaction may contain: 10× RT Buffer, d NTP mix, Reverse Transcriptase, RNA template, PCR primers, and thermostable DNA polymerase, although modifications will be known to those of skill in the art. An example of a reverse transcription reaction containing nuclease inhibitor cocktail is RETROscript™ kit (Ambion).

Example 13

Nuclease Inhibitor Cocktail Use in In Vitro Translation Reactions Using Prokaryotic and Eukaryotic Cell-Free Lysate Various prokaryotic and eukaryotic cell-free lysates may be used for protein synthesis from RNA (translation) or DNA (coupled transcription/translation) templates. Such a protein synthesis reaction may contain: buffer, salts ($Mg^{2+}$, $K^+$), amino acids, reducing agent, RNA or DNA template, energy sources (ATP, GTP), tRNAs, and a cell-free lysate (e.g., wheat germ lysate, rabbit reticulocyte lysate, *Drosophila* lysate, yeast lysate). Because of the nature of cell-free lysates, there is often a need to inhibit nucleases in cell-free extracts, and the nuclease inhibitor cocktail of the present application may be used in this regard. Components of a nuclease inhibitor cocktail for a cell-free extract may include one or more anti-nuclease antibodies that inhibit nucleases from the species from which the cell-free extract is derived.

The methods and compositions of the present invention can be used for making mRNA dependent cell-free translation systems in which a RNase is used to degrade endogenous mRNA, and the RNase is subsequently inactivated by addition of a nuclease inhibitor, including an anti-nuclease antibody to the RNase and/or a non-antibody nuclease inhibitor such as RIP.

Preparing Bacterial Cell-Free Lysates

To generate an RNase-deficient cell-free lysate from *Escherichia coli*, two approaches may be used: (1) a genetic approach, employing RNase-deletion mutants, to eliminate RNases that are non-essential for viability, in combination with (2) the antibody approach to inactivate RNases essential for viability. RNase II is a major *E. coli* exoribonuclease that accounts for up to 90% of the exoribonucleolitic activity in crude cell-free extract (Spicler and Mackie (2000)).

To provide anti-RNase antibodies for generating an RNase-deficient cell-free lysate, *E. coli* RNase II is overexpressed and purified as described by Coburn and Mackie (1996). The purified RNase II is then injected into rabbits to generate anti-RNase II antibodies as described in Example 2 above. The anti-RNase II antibodies are added to the bacterial cell-free lysate to block endogenous ribonucleases and improve in vitro protein synthesis in bacterial cell-free lysate(s). Anti-nuclease antibodies against additional *E. coli* nucleases, such as PNPase, RNase E and DNase isolated from *E. coli* lysate, are obtained in order to improve stability of the DNA template/RNA transcript.

Use of anti-nuclease antibodies is expected to dramatically improve the efficiency of in vitro transcription/translation reactions. For example, cell-free lysate obtained from MRE 600 *E. coli* stain contains many nucleases, including periplasmic RNase 1. RNase 1 is inhibited by anti-RNase 1 antibodies. Addition of 3 µg of anti-RNase 1 antibodies significantly prolonged the half-life of translated mRNA (from 2 minutes to 7.5 minutes), and at the same time increased the amount of synthesized protein by 40 to 45%.

Preparing Eukaryotic Cell-Free Lysates

A reticulocyte lysate can be prepared using nucleases, including RNase A, 1, or T1, and the specific anti-RNase antibody to the RNase.

In vitro protein synthesis is a method of producing proteins in cell-free extracts using either mRNA (translation process) or DNA (coupled transcription:translation) as a template. Rabbit reticulocyte lysate is the most popular cell-free system used for in vitro protein synthesis. This lysate contains all the macromolecular components (ribosomes, tRNAs, aminoacyl-tRNA synthetases, initiation, elongation, and termination factors, etc.) required for translation of RNAs. This crude cell-free extract also contains a large amount of globin mRNA and is known as untreated reticulocyte lysate. The endogenous globin mRNA can be removed by incubation with $Ca^{2+}$ dependent Micrococcal nuclease which is later inactivated by the chelation of $Ca^{2+}$ by EGTA. Nuclease treated reticulocyte lysate was first described by Pelham and Jackson (1976), and since then is the most popular eukaryotic cell-free expression system used in vitro translation studies. However, there are some drawbacks to this method.

An alternative to using Micrococcal nucleases with $Ca^{2+}$ followed by chelating with EGTA is to use a nuclease and an antibody that inhibits the nuclease. For example, RNase A, RNase 1, RNase T1, and even Micrococcal nuclease is used to degrade endogenous mRNAs in the cell-free lysate followed by their inactivation with specific antibodies raised against these nucleases. Antibodies are added either directly to the lysate in a liquid form and left there as inactive nuclease/antibody complex or are immobilized on the beads and after mixing with the treated lysate removed easily by centrifugation together with bound nuclease, leaving lysate nuclease-free.

This alternative method may also allow better mRNA dependent lysates to be made in other systems such as Hela cells or wheat germ. Other RNase:inhibitor couples are barnase and barstar, ribonuclease A and its specific inhibitor such as RIP or mammalian ribonucleases and their low molecular weight inhibitors (3',5'-Pyrophosphate-linked nucleotides) described by Russo and Shapiro (1999).

Preparing Microsomal Membrane Fractions

Pancreatic microsomal membranes are used to study co-translational and initial post-translational processing of proteins, such as signal peptide cleavage, membrane insertion, translocation, and core glycosylation. To assure good quality membranes, microsomes have to free from contaminating ribonucleases and be stripped of endogenous membrane-bound ribosomes and mRNA. The most popular and commercially available pancreatic microsomal membrane is canine pancreatic microsomal fraction. Isolation of the microsomal membrane fractions from other sources may be difficult due to the high content of endogenous nucleases. Membrane preparation from any other sources may be improved by use of specific antibodies to membrane associated ribonucleases and other cellular nucleases.

Example 14

Nuclease Inhibitor Cocktail as an RNA Storage Solution

It is possible to store RNA from any source in the nuclease inhibitor cocktail so as to protect the RNA from degradation. This can be achieved, for example, by adding Specific Anti-RNase Cocktail to RNase storage buffer to the final concentration of 0.5 to 1.0 U/µl (20 to 40 fold dilution).

Example 15

Non-Antibody Nuclease Inhibitors as Nuclease Inhibitor Cocktail

A combination of non-antibody nuclease inhibitors can be used to inhibit nucleases. For example, a mixture of the nuclease inhibitors $Mg^{+2}$ and spermine provided greater inhibition of RNase A activity than either $Mg^{+2}$ or spermine provided individually.

Example 16

In Vitro Translation Kit

Kits for the performance of in vitro translation which comprises at least one anti-nuclease antibody and some or all of the necessary components for, or to make, a cell-free translation system can be made according to the invention.

In vitro translation is a process of protein synthesis outside the living cell using cell-free extract and mRNA transcript as genetic material for translation. The in vitro synthesis of proteins in cell-free extracts is an important tool for molecular biologists and has a variety of applications, including the rapid identification of gene products, localization of mutations through synthesis of truncated gene products, protein folding studies, and incorporation of modified or unnatural amino acids for functional studies. The use of in vitro translation systems can have advantages over in vivo gene expression when the over-expressed product is toxic to the host cell, when the product is insoluble or forms inclusion bodies, or when the protein undergoes rapid proteolytic degradation by intracellular proteases.

Rabbit reticulocyte lysate is a highly efficient in vitro eukaryotic protein synthesis system used for translation of exogenous RNAs (either natural or generated in vitro). In vivo, reticulocytes are highly specialized cells primarily responsible for the synthesis of hemoglobin, which represents more than 90% of the protein made in the reticulocyte. These immature red cells have already lost their nuclei, but contain adequate mRNA, as well as complete translation machinery, for extensive globin synthesis. The endogenous globin mRNA may be eliminated by incubation with a nuclease inhibitor. Wheat germ extract is a convenient alternative to the rabbit reticulocyte lysate cell-free system, and the same advantages of inhibitors may be realized in it or in other systems such as the *Drosophila* extract system.

*E. coli* cell-free systems consist of a crude extract that is rich in endogenous mRNA. The extract is incubated during preparation so that this endogenous mRNA is translated and subsequently degraded. Because the level of endogenous mRNA in the prepared lysate is low, the exogenous product is easily identified. In comparison to eukaryotic systems, the *E. coli* extract has a relatively simple translational apparatus with less complicated control at the initiation level, allowing this system to be very efficient in protein synthesis. Bacterial extracts are often unsuitable for translation of RNA, because exogenous RNA is rapidly degraded by endogenous nucleases. A nuclease inhibitor may be used to inhibit the degradation of exogenous RNA in the *E. coli* system.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Allewell and Sama, "The Effect of Ammonium Sulfate on the Activity of Ribonuclease A," BIOCHEM. BIOPHYS. ACTA, 341:484–488, 1974.

Blackburn et al., "Ribonuclease Inhibitor from Human Placenta: Purification and Properties," J. BIOL. CHEM. 252:5904–5910, 1977.

Blumberg, "Creating a Ribonuclease-Free Environment," METHODS ENZYMOL. 152:20–24, 1987.

Chirgwin, et al., "Isolation of Biologically Active Ribonucleic Acid from Sources Enriched in Ribonuclease," BIOCHEMISTRY 18:5294–5299, 1979.

Chomczynski and Sacchi, "Single Step Method of RNA Isolation by Acid Guanidine Isothiocyanate-Phenol-Chloroform Extraction," ANAL. BIOCHEM. 162:156–159, 1987.

Chomczynski, "Solubolization in Formamide Protects RNA from Degradation," NUCLEIC ACIDS RES. 20:3791, 1992.

Coburn and Mackie, "Overxpression, Purification, and Properties of *Escherichia coli* Ribonuclease II," J. BIOL. CHEM. 271:1048–1053, 1996.

Gilleland and Hockett Jr., "Stability of RNA molecules stored in GITC," BIOTECHNIQUES 25:944–948, 1998.

Jocoli and Ronald, "Inhibition of Ribonuclease Activity by Bentonite," CAN. J. BIOCHEM. 51:1558–1565, 1973.

Jones, "On the Efficacy of Commonly Used Ribonuclease Inhibitors," BIOCHEM. BIOPHYS. RES. COMMUN. 69:469–474, 1976.

Lin, "Inactivation of Pancreatic Ribonuclease with Hydroxylamine-Oxygen-Curric Ion," BIOCHIM. ET BIOPHYS. ACTA 263:680–682, 1972.

Mendelsohn and Young, "Efficacy of Sodium Dodecyl Sulfate, Diethyl Pyrocarbonate, Proteinase K and Heparin Using a Sensitive Ribonuclease Assay," BIOCHIM. ET BIOPHYS. ACTA 519:461–473, 1978.

Murphy et al., "A Potent, Cost-Effective RNase Inhibitor," BIOTECHNIQUES 18:1068–1073, 1995.

Pelham and Jackson, EUR. J. BIOCHEM. 67:247–256, 1976.

Russo and Shapiro, "Potent Inhibition of Mammalian Ribonucleases by 3' 5'-Pyrophosphate-linked Nucleotides," J. BIOL. CHEM. 274:14,902–14,908, 1999.

Sambrook, et al., "Molecular Cloning, A Laboratory Manual," pp. 7.16–7.52, 1989.

Spackman et al., "The Disulfide Bonds of Ribonuclease," J. BIOL. CHEM. 235:648–659, 1960.

Spicler and Mackie, "Action of RNase II and Polynucleotide Phosphorylase against RNAs Containing Stem-Loops of Defined Structure," J. BACTERIOLOGY 182(9): 2422–2427, 2000.

Wolf et al., "A Mechanism of the Irreversible Inactivation of Bovine Pancreatic Ribonuclease by Diethylpyrocarbonate," EUR. J. BIOCHEM. 13:519–525, 1970.

Wu, et al., "Methods in Gene Biotechnology," CRC Press, Boca Raton, Fla., pp. 29–56, 1997.

Zale and Klibanov, "Why Does Ribonuclease Irreversibly Inactivated at High Temperature?," BIOCHEMISTRY 25:5432–5444, 1986.

What is claimed is:

1. A method comprising:
   a) obtaining at least a first nuclease inhibitor further defined as a soluble anti-nuclease antibody;
   b) obtaining at least a second nuclease inhibitor further defined as a non-antibody nuclease inhibitor;

c) obtaining a composition; and
d) admixing the first nuclease inhibitor, the second nuclease inhibitor, and the composition to form an admixture;
wherein nucleases that may be present in the admixture are inhibited.

2. The method of claim 1, wherein admixing is further defined as comprising mixing the first and second nuclease inhibitors to form a nuclease inhibitor cocktail and mixing the nuclease inhibitor cocktail with the composition.

3. The method of claim 1, wherein obtaining the first and second nuclease inhibitors comprises obtaining a nuclease inhibitor cocktail comprising the first nuclease inhibitor and the second nuclease inhibitor.

4. The method of claim 1, wherein the composition comprises at least one nuclease.

5. The method of claim 1, wherein the composition comprises RNA.

6. The method of claim 1, wherein the composition is further defined as an in vitro translation reaction.

7. The method of claim 1, wherein the composition is a reagent used in molecular biology.

8. The method of claim 1, wherein the soluble anti-nuclease antibody is a polyclonal antibody.

9. The method of claim 1, wherein the soluble anti-nuclease antibody is an anti-ribonuclease antibody.

10. The method of claim 9, wherein the soluble anti-ribonuclease antibody is capable of binding to one or more of RNase A, a member of the RNase A family, RNase B, RNase C, RNase 1, RNase T1, RNase T2, RNase L, a member of the RNase H family, a member of the angiogenin RNase family, eosinophil RNase, a micrococcal nuclease, a member of the mammalian ribonuclease 1 family, a member of the ribonuclease 2 family, a messenger RNA ribonuclease, 5'-3' exoribonuclease, 3'-5' exoribonuclease, a decapping enzyme, a deadenylase, RNase P, RNase III, RNase B, RNase I,I*, RNase HI, RNase HII, RNase M, RNase R, RNase IV, F; RNase P2,O, PIV, PC, RNase N, RNase II, PNPase, RNase D, RNase BN, RNase T, RNase PH, OligoRNase, RNase R, RNase Sa, RNase F1, RNase U2, RNase Ms, or RNase St.

11. The method of claim 10, wherein the soluble anti-ribonuclease antibody is an anti-RNase A antibody.

12. The method of claim 10, wherein the soluble anti-ribonuclease antibody is an anti-RNase 1 antibody.

13. The method of claim 10, wherein the soluble anti-ribonuclease antibody is an anti-RNase T1 antibody.

14. The method of claim 1, wherein the soluble anti-nuclease antibody is an anti-deoxyribonuclease antibody.

15. The method of claim 1, wherein soluble anti-nuclease antibody is capable of binding to S1 nuclease or micrococcal nuclease.

16. The method of claim 1, wherein the second nuclease inhibitor is human placental ribonuclease inhibitor, a bovine ribonuclease inhibitor, a porcine ribonuclease inhibitor, diethyl pyrocarbonate, ethanol, formamide, guanidinium thiocyanate, vanadyl-ribonucleoside complexes, macaloid, sodium dodecyl sulfate, ethylenediamine tetraacetic acid, proteinase K, heparin, hydroxylamine-oxygen-cupric ion, bentonite, ammonium sulfate, dithiothreitol, β-mercaptoethanol, cysteine, dithioerythritol, tris (2-carboxyethyl) phosphene hydrochloride, $Mg^{+2}$, $Mn^{+2}$, $Zn^{+2}$, $Fe^{+2}$, $Ca^{+2}$, or $Cu^{+2}$.

17. The method of claim 16, wherein the nuclease inhibitor is human placental ribonuclease inhibitor.

18. The method of claim 1, further defined as a method of inhibiting nucleases in the composition.

19. A method of performing a molecular biology technique comprising;
a) obtaining at least a first nuclease inhibitor further defined as a soluble anti-nuclease antibody;
b) obtaining at least a second nuclease inhibitor further defined as a non-antibody nuclease inhibitor;
and using the first and second nuclease inhibitors in the molecular biology technique.

20. The method of claim 19, wherein the molecular biology technique is further defined as RNA isolation, mRNA purification, RNA storage, northern blotting, a nuclease protection assay, Reverse Transcriptase-Polymerase Chain Reaction, an in vitro translation reaction, an in vitro transcription reaction, or an in vitro coupled transcription/translation reaction.

21. The method of claim 19, wherein the molecular biology technique is further defined as a technique of using or making RNA, DNA, or both RNA and DNA.

22. The method of claim 19, wherein the soluble anti-nuclease antibody is a soluble anti-ribonuclease antibody.

23. The method of claim 19, wherein the soluble anti-nuclease antibody is a soluble anti-deoxyribonuclease antibody.

24. The method of claim 19, wherein the soluble anti-nuclease antibody is capable of binding to S1 nuclease or micrococcal nuclease.

25. The method of claim 19, further defined as comprising obtaining a nuclease inhibitor cocktail comprising at least the soluble anti-nuclease antibody and the second nuclease inhibitor and using the cocktail in the molecular biology technique.

26. The method of claim 19, wherein the second nuclease inhibitor is human placental ribonuclease inhibitor, a bovine ribonuclease inhibitor, a porcine ribonuclease inhibitor, diethyl pyrocarbonate, ethanol, formamide, guanidinium thiocyanate, vanadyl-ribonucleoside complexes, macaloid, sodium dodecyl sulfate, ethylenediamine tetraacetic acid, proteinase K, heparin, hydroxylamine-oxygen-cupric ion, bentonite, ammonium sulfate, dithiothreitol, β-mercaptoethanol, cysteine, dithioerythritol, tris (2-carboxyethyl) phosphene hydrochloride, $Mg^{+2}$, $Mn^{+2}$, $Zn^{+2}$, $Fe^{+2}$, $Ca^{+2}$, or $Cu^{+2}$.

27. The method of claim 19, further defined as obtaining a lysate and employing the lysate in the molecular biology technique.

28. The method of claim 26, wherein the second nuclease inhibitor is human placental ribonuclease inhibitor.

29. The method of claim 19, wherein the soluble anti-nuclease antibody is an anti-ribonuclease antibody.

30. The method of claim 29, wherein the soluble anti-ribonuclease antibody is capable of binding to one or more of RNase A, a member of the RNase A family, RNase B, RNase C, RNase 1, RNase T1, RNase T2, RNase L, a member of the RNase H family, a member of the angiogenin RNase family, eosinophil RNase, a micrococcal nuclease, a member of the mammalian ribonuclease 1 family, a member of the ribonuclease 2 family, a messenger RNA ribonuclease, 5'-3' exoribonuclease, 3'-5' exoribonuclease, a decapping enzyme, a deadenylase, RNase P, RNase III, RNase B, RNase I,I*, RNase HI, RNase HII, RNase M, RNase R, RNase IV, F; RNase P2,O, PIV, PC, RNase N, RNase II, PNPase, RNase D, RNase BN, RNase T, RNase PH, OligoRNase, RNase R, RNase Sa, RNase F1, RNase U2, RNase Ms, or RNase St.

31. The method of claim 30, wherein the soluble anti-ribonuclease antibody is an anti-RNase A antibody.

32. The method of claim 30, wherein the soluble anti-ribonuclease antibody is an anti-RNase 1 antibody.

33. The method of claim 30, wherein the soluble anti-ribonuclease antibody is an anti-RNase T1 antibody.

34. The method of claim 19, wherein the soluble anti-nuclease antibody is an anti-deoxyribonuclease antibody.

35. The method of claim 19, wherein soluble anti-nuclease antibody is capable of binding to S1 nuclease or micrococcal nuclease.

36. A method comprising:
   a) obtaining at least a first nuclease inhibitor further defined as a soluble anti-nuclease antibody;
   b) obtaining at least a second nuclease inhibitor;
   c) obtaining a composition; and
   d) admixing the first nuclease inhibitor, the second nuclease inhibitor, and the composition to form an admixture;
   wherein nucleases that may be present in the admixture are inhibited and wherein the composition is further defined as an in vitro translation reaction.

37. A method comprising:
   a) obtaining at least a first nuclease inhibitor further defined as a soluble anti-nuclease antibody;
   b) obtaining at least a second nuclease inhibitor;
   c) obtaining a composition; and
   d) admixing the first nuclease inhibitor, the second nuclease inhibitor, and the composition to form an admixture;
   wherein nucleases that may be present in the admixture are inhibited and wherein the soluble anti-nuclease antibody is an anti-ribonuclease antibody capable of binding to one or more of RNase A, a member of the RNase A family, RNase B, RNase C, RNase 1, RNase T1, RNase T2, RNase L, a member of the RNase H family, a member of the angiogenin RNase family, eosinophil RNase, a micrococcal nuclease, a member of the mammalian ribonuclease 1 family, a member of the ribonuclease 2 family, a messenger RNA ribonuclease, 5'-3' exoribonuclease, 3'-5' exoribonuclease, a decapping enzyme, a deadenylase, RNase P, RNase III, RNase B, RNase I,I*, RNase HI, RNase HII, RNase M, RNase R, RNase IV, F; RNase P2,O, PIV, PC, RNase N, RNase II, PNPase, RNase D, RNase BN, RNase T, RNase PH, OligoRNase, RNase R, RNase Sa, RNase F1, RNase U2, RNase Ms, or RNase St.

38. The method of claim 37, wherein the soluble anti-ribonuclease antibody is an anti-RNase A antibody.

39. The method of claim 37, wherein the soluble anti-ribonuclease antibody is an anti-RNase 1 antibody.

40. The method of claim 37, wherein the soluble anti-ribonuclease antibody is an anti-RNase T1 antibody.

41. A method of performing a molecular biology technique comprising obtaining a first nuclease inhibitor further defined as a soluble anti-nuclease antibody, and using the soluble anti-nuclease antibody in the molecular biology technique, wherein the molecular biology technique is further defined as RNA isolation, mRNA purification, RNA storage, northern blotting, a nuclease protection assay, Reverse Transcriptase-Polymerase Chain Reaction, an in vitro translation reaction, an in vitro transcription reaction, or an in vitro coupled transcription/translation reaction.

42. A method of performing a molecular biology technique comprising: obtaining a first nuclease inhibitor further defined as a soluble anti-nuclease antibody; obtaining a lysate; and using the soluble anti-nuclease antibody and the lysate in the molecular biology technique.

* * * * *

UNITED STATES PATENT AND TRADEMARK OFFICE
CERTIFICATE OF CORRECTION

| | | |
|---|---|---|
| PATENT NO. | : 7,163,793 B2 | Page 1 of 1 |
| APPLICATION NO. | : 10/675860 | |
| DATED | : January 16, 2007 | |
| INVENTOR(S) | : Kudlicki et al. | |

It is certified that error appears in the above-identified patent and that said Letters Patent is hereby corrected as shown below:

In claim 10, column 29, line 36, delete "RNase B" and insert --RNase E-- therefor.

In claim 30, column 30, line 60, delete "RNase B" and insert --RNase E-- therefor.

In claim 37, column 32, line 7, delete "RNase B" and insert --RNase E-- therefor.

In claim 19, column 30, line 2, delete "comprising;" and insert/replace --comprising:-- therefor.

Signed and Sealed this

Seventeenth Day of April, 2007

JON W. DUDAS
*Director of the United States Patent and Trademark Office*